United States Patent [19]
Suzuki et al.

[11] Patent Number: 6,013,676
[45] Date of Patent: Jan. 11, 2000

[54] AGRICULTURAL CHEMICAL COMPOSITION WITH IMPROVED RAINDROP RESISTANCE

[75] Inventors: Masahiro Suzuki, Shizuoka; Michio Tani, Toyama; Keiichi Sato, Shizuoka, all of Japan

[73] Assignee: Nippon Soda Co., Ltd., Tokyo, Japan

[21] Appl. No.: 09/011,224

[22] PCT Filed: Jun. 6, 1997

[86] PCT No.: PCT/JP97/01924

§ 371 Date: Feb. 9, 1998

§ 102(e) Date: Feb. 9, 1998

[87] PCT Pub. No.: WO97/46092

PCT Pub. Date: Dec. 11, 1997

[30] Foreign Application Priority Data

Jun. 7, 1996 [JP] Japan ................................. 8-166674

[51] Int. Cl.$^7$ ................................................. A01N 33/24
[52] U.S. Cl. .......................................................... 514/640
[58] Field of Search ............................ 504/116; 514/640

[56] References Cited

U.S. PATENT DOCUMENTS

| | | | |
|---|---|---|---|
| 4,324,781 | 4/1982 | Okamoto et al. | 424/78 |
| 5,317,004 | 5/1994 | Misselbrook et al. | 504/116 |
| 5,360,783 | 11/1994 | Itoh et al. | 504/305 |
| 5,462,714 | 10/1995 | Talwalker et al. | 422/37 |

FOREIGN PATENT DOCUMENTS

| | | |
|---|---|---|
| 0 456 198 | 11/1991 | European Pat. Off. |
| 0 498 755 | 8/1992 | European Pat. Off. |
| 55-167204 | 12/1980 | Japan |
| 56-92207 | 7/1981 | Japan |
| 62-252702 | 11/1987 | Japan |
| 1-190610 | 7/1989 | Japan |
| 2-45405 | 2/1990 | Japan |
| 3-11003 | 1/1991 | Japan |
| 7-252103 | 10/1995 | Japan |
| 63-270607 | 11/1998 | Japan |
| 9619442 A1 | 6/1996 | WIPO |

Primary Examiner—Jose' G. Dees
Assistant Examiner—Alton Pryor
Attorney, Agent, or Firm—Jacobson, Price, Holman & Stern, PLLC

[57] ABSTRACT

The present invention is directed to a pesticide composition with improved raindrop resistance characterized in that it contains 0.1–70% by weight of a pesticidal component and 10–50% by weight of sorbitan trioleate relative to the weight of the pesticide composition.

11 Claims, No Drawings

AGRICULTURAL CHEMICAL COMPOSITION WITH IMPROVED RAINDROP RESISTANCE

This application is a 371 of PCT/JP97/01924 filed Jun. 6, 1992.

FIELD OF THE INVENTION

The present invention relates to an agricultural chemical composition with remarkably-improved raindrop resistance, comprising a pesticidal component and sorbitan trioleate.

BACKGROUND ART

Active ingredient components useful as a pesticide, such as insecticides and fungicides, have been prepared into a formulation, such as emulsifiable concentrate, emulsion, wettable powder, suspension and water dispersible granule, depending upon their physicochemical properties and the objective to use them practically in agricultural crop fields. In order to supplement the deterioration of long-lasting activity of pesticidal components, which might be caused by any reason such as dilution of the pesticidal components on the surface of plant leaves due to the growth of the leaves themselves, photodegradation of the pesticidal components on the surface of leaves, and carrying away of pesticidal components from the surface of leaves due to rainfalls, etc., and exceeding degree of pesticide application has been performed onto agricultural crops for minimizing their damages caused by pest insects and plant diseases and for keeping the quality of cultivated crops. However, such exceeding degree of pesticide application has imposed a burden not only in terms of laboring and economical point of view but also caused environmental pollution.

Therefore, various efforts to find out the means to reduce the amount of pesticides used in the environment have been made. As a method to prevent the deterioration in efficacy of a pesticide due to rainfalls, a method to prepare a pesticide composition for coating use having good raindrop resistance by containing α-starch therein is disclosed in Japanese Patent Laid-open No. Sho 54-80423 Gazette, and a wettable powder formulation of which raindrop resistance being improved by an incorporation of a resin in powder therein is disclosed in Japanese Patent Laid-open No. Sho 59-172401 Gazette, and a water dispersible granule with improved-raindrop resistance prepared by incorporating polyvinyl alcohol, carboxymethylcellulose, etc. therein to enhance sticking property is disclosed in Japanese Patent Laid-open No. Hei 2-40301 Gazette, for example.

Whereas, in Japanese Patent Laid-open No. Hei 1-190610 Gazette, a pesticide composition containing 1–10% by weight of sorbitan trioleate is disclosed. However, no description has been made yet on a pesticide composition which contains high content of sorbitan trioleate as much as 10–50% by weight for aiming at improving its raindrop resistance.

DISCLOSURE OF THE INVENTION

It is an object of the present invention to provide a pesticide composition having excellent long-lasting activity by means of improving the raindrop resistance of a pesticide composition on surface of plant leaves, in complying to a request to prolong the activity-continuance period of pesticide compositions.

As a result that the inventors of the present invention had attempted to accomplish such object, they have found out that pesticide formulations, such as an emulsifiable concentrate, an emulsion, a wettable powder, a suspension concentrate and a water dispersible granule, wherein 10–50% by weight of sorbitan trioleate relative to the weight of a whole pesticide component is incorporated, show to have excellent raindrop resistance, whereby they have accomplished the present invention.

Therefore, the present invention is now described in detail in the following.

The present invention is directed to (1) a pesticide composition containing 0.1–70% by weight of a pesticidal component and 10–50% by weight of sorbitan trioleate, relative to the weight of the whole pesticide composition, (2) an emulsifiable concentrate containing 0.1–70% by weight of a pesticidal component, 1–30% by weight of an emulsifier, 10–50% by weight of sorbitan trioleate and a solvent, relative to the weight of the whole emulsifiable concentrate, (3) an emulsion containing 0.1–70% by weight of a pesticidal component, 1–30% by weight of an emulsifier, 10–30% by weight of sorbitan trioleate, water and a nonpolar solvent, relative to the weight of the whole emulsion, (4) a wettable powder containing 0.1–70% by weight of a pesticidal component, 0.1–10% by weight of a wetting agent, 0.5–20% by weight of a dispersing agent, 10–50% by weight of sorbitan trioleate and a filler, relative to the weight of the whole wettable powder formulation, (5) a suspension concentrate containing 0.1–70% by weight of a pesticidal component, 0.1–10% by weight of a wetting agent, 0.5–20% by weight of a dispersing agent, 10–50% by weight of sorbitan trioleate and water, relative to the weight of the whole suspension concentrate, and (6) a water dispersible granule containing 0.1–70% by weight of a pesticidal component, 0.1–10% by weight of a wetting agent, 0.5–20% by weight of a dispersing agent, 10–30% by weight of sorbitan trioleate and a filler, relative to the weight of the whole water dispersible granule.

Any compounds having pesticidal activity and appropriate physicochemical properties suitable for producing respective type of formulations can be used as the pesticidal component specified in the present invention without any limitation. For the example of the active component to be used for an emulsifiable concentrate and an emulsion in the present invention, the ones soluble in organic solvents, such as triflumizole, fluazinam, pefurazoate, prochloraz, propiconazole, mycrobutanil, triadimefon, bitertanol, imazalil, fenarimol, thiabendazole and benzamidoxime compounds represented by a general formula (1);

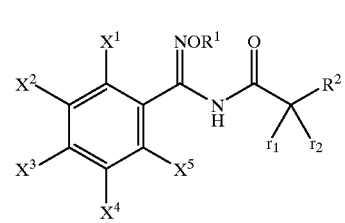

wherein $R^1$ is optionally substituted $C_1$–$C_4$ alkyl, optionally substituted $C_2$–$C_4$ alkenyl or optionally substituted $C_2$–$C_4$ alkynyl, $R^2$ is optionally substituted phenyl or optionally substituted heterocycle, $X^1$ is $C_1$–$C_4$ haloalkyl, $X^2$, $X^3$, $X^4$ and $X^5$ are each independently hydrogen, a halogen atom, $C_1$–$C_4$ alkyl, $C_1$–$C_4$ haloalkyl, $C_1$–$C_4$ alkoxy, $C_1$–$C_4$ haloalkoxy, $C_1$–$C_4$ alkylthio, $C_1$–$C_4$ alkylsulfinyl, $C_1$–$C_4$ alkylsulfonyl, nitro, amino or $C_1$–$C_4$ alkylcarbonylamino, $r_1$ and $r_2$ are each independently hydrogen, a halogen atom, $C_1$–$C_4$ alkyl, $C_1$–$C_4$ haloalkyl, $C_1$–$C_4$ alkoxy, $C_1$–$C_4$ alkylthio or amino, or $r_1$ and $r_2$ may jointly form a carbonyl group, which are disclosed in WO96/19442 Gazette by the applicant of the present invention, can be given.

Definitive examples for the compounds represented by the general formula (1) are shown in Table 1.

TABLE 1

[Structure: benzene ring with substituents $CF_3$, $X^2$, $X^3$, $X^4$, $X^5$, and side chain $C(=NOR^1)-NH-C(=O)-C(r_1)(r_2)-R_2$]

($r_1, r_2$ = H)

| No. | $X_2$ | $X_3$ | $X_4$ | $X_5$ | $R_1$ | $R_2$ |
|---|---|---|---|---|---|---|
| 1 | H | H | F | F | $CH_2$–cyclopropyl | Ph |
| 2 | H | H | Cl | F | $CH_2$–cyclopropyl | Ph |
| 3 | H | H | F | Cl | $CH_2$–cyclopropyl | Ph |
| 4 | H | H | Cl | Cl | $CH_2$–cyclopropyl | Ph |
| 5 | H | H | F | F | $CH_2$–cyclopropyl | 2-F-Ph |
| 6 | H | H | Cl | F | $CH_2$–cyclopropyl | 2-F-Ph |
| 7 | H | H | F | Cl | $CH_2$–cyclopropyl | 2-F-Ph |
| 8 | H | H | Cl | Cl | $CH_2$–cyclopropyl | 2-F-Ph |
| 9 | H | H | F | F | $CH_2$–cyclopropyl | 2-F-5-Me-Ph |
| 10 | H | H | Cl | F | $CH_2$–cyclopropyl | 2-F-5-Me-Ph |
| 11 | H | H | F | Cl | $CH_2$–cyclopropyl | 2-F-5-Me-Ph |
| 12 | H | H | Cl | Cl | $CH_2$–cyclopropyl | 2-F-5-Me-Ph |
| 13 | H | H | F | F | $CH_2CH_2Cl$ | Ph |
| 14 | H | H | Cl | F | $CH_2CH_2Cl$ | Ph |
| 15 | H | H | F | Cl | $CH_2CH_2Cl$ | Ph |
| 16 | H | H | Cl | Cl | $CH_2CH_2Cl$ | Ph |
| 17 | H | 11 | F | F | $CH_2CH_2Cl$ | 2-F-Ph |
| 18 | H | H | Cl | F | $CH_2CH_2Cl$ | 2-F-Ph |
| 19 | H | H | F | Cl | $CH_2CH_2Cl$ | 2-F-Ph |
| 20 | 11 | H | Cl | Cl | $CH_2CH_2Cl$ | 2-F-Ph |
| 21 | H | H | F | F | $CH_2CH_2Cl$ | 2-F-5-Me-Ph |
| 22 | H | H | Cl | F | $CH_2CH_2Cl$ | 2-F-5-Me-Ph |
| 23 | H | H | F | Cl | $CH_2CH_2Cl$ | 2-F-5-Me-Fh |
| 24 | H | H | Cl | Cl | $CH_2CH_2Cl$ | 2-F-5-Me-Ph |

Although there is no particular limitation in the content of the pesticidal component for incorporating in a formulation, the content should be less than which may cause the precipitation in crystal of the pesticidal component during the preservation time at around –10° C.

As the pesticidal component used in a wettable powder and a suspension concentrate, the one having a higher melting point, such as triflumizole, fluazinam, propiconazole, hexythiazox, oxolinic acid, thiophanate-methyl, thiuram and benzamidoxime compounds represented by a general formula (1) and exemplified in Table 1, which was disclosed in WO96/19442 Gazette by the inventors of the present invention, are given as the examples. Although there is no specific limitation in the content of the pesticidal component to be incorporated in a formulation, it is preferable to take a content in a range less than 70% by weight.

Whereas, for water dispersible granule, as the pesticidal component, it is preferable to use the one of which melting point is higher than 120° C., such as thiophanate-methyl, if spray drier method is employed, while it is preferable to use the one which are in solid at an ambient temperature, such as triflumizole, fluazinam, propiconazole, hexythiazox, oxolinic acid, thiophanate-methyl, thiuram and benzamidoxime compounds represented by a general formula (I) and exemplified in Table 1, which are disclosed in WO96/19442 Gazette by the inventors of the present invention, if either agitation method or extrusion method is employed. Although there is no specific limitation in the content of the pesticidal component to be incorporated in a formulation, it is preferable to take a content in a range less than 70% by weight.

In the present invention, surfactants are used in various ways. In case of an emulsifiable concentrate and an emulsion, as such emulsifier, alkyl phenyl ethers added thereon with polyoxyethylene, alkyl ethers added thereon with polyoxyethylene, higher fatty acid esters added thereon with polyoxyethylene, etc. are given as the examples, and these compounds can be used either alone or in a mixture of more than 2 of them.

In an emulsifiable concentrate and an emulsion, a protective colloid agent in an amount of 0.1–10% by weight may be added into the formulation for improving the stability of the emulsified solution prepared by their dilution. For the examples of such protective colloid agent, nonionic surfactants such as sorbitan higher fatty acid esters added thereon with polyoxyethylene, tristyryl phenyl ether added thereon with polyoxyethylene, etc. and alkyl phenyl ether sulfates added thereon with polyoxyethylene, alkylbenzenesulfonates, higher alcohol sulfates, etc. can be given, and these compounds can be used either alone or in a mixture of more than 2 of them.

In wettable powders, suspension concentrates and water dispersible granule, as the wetting agent and the dispersing agent, alkylnaphthalene sulfonates, alkylbenzenesulfonates, tristyryl phenyl ether added thereon with polyoxyethylene, polycarboxylates, ligninsulfonates, formaldehyde condensates of alkylnaphthalenesulfonates, isobutylene-maleic anhydride copolymer, etc. can be give as the examples, and these compounds can be used either alone or in a mixture of more than 2 of them.

As the example for the solvent to be used in the present invention, petrolic straight chain hydrocarbons, such as Isopar-L, Isopar-V and Exxsol D-100 (Produced by Exxon Chemicals Co., Ltd.), petrolic aromatic hydrocarbons, such as Solvesso 100, Solvesso 150 and Solvesso 200 (Produced by Exxon Chemicals Co., Ltd.), nonpolar solvents comprising esters of vegetable oils and their hydrolized products, such as Excepart MC and Excepart L-OL (Produced by Kao Co., Ltd.) and polar solvents, such as cyclohexane, N-methylpyrrolidone and dimethyl sulfoxide, can be given, and these compounds can be used either alone or in a mixture of more than 2 of them.

As the examples for the filler usable in the present invention, inorganic salts, such as potassium chloride, potassium carbonate, phosphates, hydrogenphosphates, ammonium sulfate and urea, diatomaceous earth, such as Kunilite 201 and Kunilite B-106 (Produced by Kunimine Industries Co., Ltd.), pyrophyllite-type clay, such as SA-M clay (Produced by Kanto Bentonite Co., Ltd.), and kaolinite-type clay, such as Zeaklite AT (Produced by Zeaklite Co., Ltd.), can be given, and these compounds can be used either alone or in a mixture of more than 2 of them.

A filler with high oil-absorption property means a substance which can absorb sorbitan trioleate, and diatomaceous earth, silicon oxide and the like can be give as the example, these materials can be used either alone or in a mixture of more than 2 of them.

In addition, an antifreezing agent may be added into the pesticide composition according to the present invention, particularly into the special formulations to be provided for cold districts. As the examples for the antifreezing agent, ethylene glycol, propylene glycol, glycerol and the like are given, and these materials can be used either alone or in a mixture of more than 2 of them.

Whereas, for a purpose of preventing the precipitation and separation of the particles of the pesticidal component in an emulsion and a suspension concentrate and the separation of emulsified-particles of sorbitan trioleate, a thickener, such as an alkyl cellulose, a hydroxyalkyl cellulose, a carboxymethyl celluloses and its metal salt, polyvinyl alcohol and natural rubber, may be added into the pesticide composition of the present invention.

Although the incorporating rate for each components in the pesticide composition according to the present invention differs depending upon the type of the pesticidal component, however, an emulsifiable concentrate normally contains 0.1–70% by weight and preferably 0.1–30% by weight of a pesticidal component, 1–30% by weight and preferably 5–15% by weight of an emulsifier and a protective colloid agent, 20–80% by weight and preferably 30–70% by weight of a solvent, and 10–50% by weigh and preferably 10–20% by weight of sorbitan trioleate, relative to the weight of the whole emulsifiable concentrate. For an emulsion, it normally contains 0.1–70% by weight and preferably 0.1–30% by weight of a pesticidal component, 1–30% by weight and preferably 5–15% by weight of an emulsifier and a protective colloid agent, 80% by weight or less and preferably 30% by weight or less of a solvent, 10–50% by weight and preferably 10–20% by weight of sorbitan trioleate, and 20–80% by weight and preferably 50–80% by weight of water, relative to the weight of the whole emulsion.

For a wettable powder, it normally contains 0.1–70% by weight and preferably 0.1–50% by weight of a pesticidal component, 0.6–30% by weight and preferably 5–15% by weight of a wetting agent and a dispersing agent, 20–80% by weight and preferably 30–70% by weight of a filler, and 10–30% by weight and preferably 10–20% by weight of sorbitan trioleate, relative to the weight of the whole emulsion. For a suspension concentrate, it normally contains 0.1–70% by weight and preferably 0.1–30% by weight of a pesticidal component, 0.6–30% by weight and preferably 5–15% by weight of a wetting agent and a dispersing agent, 10–50% by weight and preferably 10–20% by weight of sorbitan trioleate, and 20–80% by weight and preferably 50–80% by weight of water, relative to the weight of the whole emulsion. For a water dispersible granule, it normally contains 0.1–70% by weight and preferably 0.1–50% by weight of a pesticidal component, 0.6–30% by weight and preferably 5–15% by weight of a wetting agent and a dispersing agent, 20–80% by weight and preferably 30–70% by weight of a filler, and 10–30% by weight and preferably 10–20% by weight of sorbitan trioleate, relative to the weight of the whole emulsion.

As formulation types of the pesticide composition according to the present invention, an emulsifiable concentrate, an emulsion, a wettable powder, a suspension concentrate, a water dispersible granule, etc. can be exemplified. An emulsifiable concentrate is prepared by dissolving a pesticidal component, an emulsifier and sorbitan trioleate, and also a protective colloid agent if appropriate, into a solvent. An emulsion is prepared by dissolving a pesticidal component, an emulsifier and sorbitan trioleate, and also a protective colloid agent if appropriate, into a solvent, and adding water to the solution obtained to produce emulsified particles by using an emulsifier. In this method, an antifreezing agent may be added to water when it is necessary. A wettable powder is prepared by firstly producing high oil-adsorbent filler in which sorbitan trioleate being adsorbed, admixing a pesticidal component, a wetting agent, a dispersing agent and the filler described above, and allowing the mixture obtained to dry milling process to micronize the pesticidal component and the filler up to an average particle size of 20 µm or less.

A suspension concentrate is prepared by admixing a pesticidal component, a wetting agent, a dispersing agent, an antifreezing agent, water and sorbitan trioleate, and subsequently allowing the mixture obtained to wet milling process to micronize the pesticidal component and the filler up to an average particle size of 20 µm or less, and further emulsifying sorbitan trioleate. Alternatively, a suspension concentrate is prepared by admixing a pesticidal component, a wetting agent, a dispersing agent, an antifreezing agent and water, and subsequently allowing the mixture obtained to wet milling process to micronize the pesticidal component up to an average particle size of 10 µm or less, adding sorbitan trioleate and emulsifying the mixture by using an emulsifier. In spray dryer method, a water dispersible granule is prepared by admixing a pesticidal component, a wetting agent, a dispersing agent, water and sorbitan trioleate, then allowing the mixture obtained to wet milling process to micronize the pesticidal component up to an average particle size of 20 µm or less, emulsifying sorbitan trioleate and preparing the water dispersible granite by using a spray dryer equipment. Whereas, in agitation method or extrusion method, a water dispersible granule is prepared by firstly producing high oil-adsorbent filler in which sorbitan trioleate being adsorbed, admixing a pesticidal component, a wetting agent, a dispersing agent and the filler prepared above, allowing the mixture obtained to dry milling process to micronize the pesticidal component and the filler up to an average particle size of 20 µm or less and preparing the water dispersible granule by using either a agitation equipment or an extrusion equipment.

BEST MODE FOR CARRYING OUT THE INVENTION

EXAMPLES

Now, the present invention is further described in detail with referring the examples described hereinbelow. However, it should be noted that the present invention shall not be limited to the scope described in the following examples.

Example 1

Triflumizole in an amount of 160 g was dissolved in a mixed solvent consisting of a petrolic solvent, Solvesso 150 in an amount of 470 g and cyclohexanone in an amount of 100 g, and the solution obtained was further added with nonyl phenyl ether added thereon with oxyethylene in an amount of 100 g, dodecylbenzenesulfonate calcium salt in an amount of 20 g and sorbitan trioleate in an amount of 150 g, and was dissolved while heating to prepare an emulsifiable concentrate.

Example 2

Triflumizole in an amount of 110 g was dissolved in a petrolic solvent, Solvesso 150 in an amount of 330 g, and the solution obtained was further added with sorbitan monooleate added thereon with oxyethylene in an amount of 80 g, calcium dodecylbenzenesulfonate in an amount of 10 g and sorbitan trioleate in an amount of 100 g, and was dissolved while heating. The solution obtained was added into distillated water in an amount of 320 g wherein glycerol in an amount of 50 g being dissolved, and the resulting mixture was emulsified by using Polytron to prepare an emulsion.

Example 3

Triflumizole in an amount of 160 g was admixed with sodium dioctylsulfosuccinate in an amount of 300 g, sodium ligninsulfonate in an amount of 100 g and clay in an amount of 310 g, sorbitan trioleate in an amount of 150 g adsorbed in a mixture of diatomaceous earth in an amount of 150 g and silicon oxide in an amount of 100 g, and the mixture obtained was then allowed to dry milling process by using a horizontal jet mill (diameter: 3.5 inches) to prepare a wettable powder formulation.

Example 4

Triflumizole in an amount of 160 g, tristyryl phenyl ether added thereon with oxyethylene in an amount of 40 g, polycarboxylate sodium salt in an amount of 20 g, glycerol in an amount of 100 g, silicon-containing defoamer in an amount of 10 g and sorbitan trioleate in an amount of 150 g were added to distilled water in an amount of 520 g and then mixed, and the mixture obtained was then allowed to wet milling process using Eiger Motor Mill (Produced by Eiger Japan K.K.), wherein zircon beads with a diameter of 1 mm are used, to prepare a suspension concentrate.

Example 5

Triflumizole in an amount of 330 g was admixed with sodium dodecylbenzenesulfonate in an amount of 300 g, a formaldehyde condensate of a sodium alkylnaphthalenesulfonate in an amount of 70 g, sodium ligninsulfonate in an amount of 60 g, a mixture of a calcium salt and a sodium salt of a higher fatty acid in an amount of 5 g and sodium chloride in an amount of 105 g, sorbitan trioleate in an amount of 100 g adsorbed to diatomaceous earth in an amount of 300 g, then the mixture obtained was allowed to dry milling process using a horizontal jet mill (diameter: 3.5 inches). The pulverized product was then added with distillated water in an amount of 330 g, kneaded by using Bench Kneader (Manufactured by Irie Shokai K.K.) and prepared into noodle-shaped wet granules having a diameter of 0.6 mm by using Micro-type Granulating Machine (Manufactured by Tsutsui Rikagaku Kikai K.K.). The granules obtained was then dried by using a fan dryer at 40° C. for 12 hours to obtain a water dispersible granule.

Example 6

The compound No. 1 in Table 1 in an amount of 110 g was dissolved in a mixed solvent of petrolic solvent, Solvesso 200 in an amount of 570 g and N-methylpyrrolidone in an amount of 100 g, and the solution obtained was further added with tristyryl phenyl ether added thereon with oxyethylene in an amount of 100 g, tristyryl phenyl ether phosphate added thereon with oxyethylene in an amount of 20 g and sorbitan trioleate in an amount of 100 g, and was dissolved while heating to prepare an emulsifiable concentrate.

Example 7

The compound No. 1 in Table 1 in an amount of 55 g was dissolved in a petrolic solvent, Solvesso 200 in an amount of 330 g, and the solution obtained was further added with tristyryl phenyl ether added thereon with oxyethylene in an amount of 100 g and sorbitan trioleate in an amount of 100 g, and was dissolved while heating. The solution obtained was then added to distilled water in an amount of 315 g wherein glycerol in an amount of 100 g being dissolved, and the resulting mixture was emulsified by using Polytron to prepare an emulsion.

Example 8

The compound No. 1 in Table 1 in an amount of 110 g was admixed with sodium laurylsulfate in an amount of 70 g, sodium ligninsulfonate in an amount of 100 g, a formaldehyde condensate of a sodium alkylnaphthalene sulfonate in an amount of 50 g and clay in an amount of 270 g, sorbitan trioleate in an amount of 100 g adsorbed to diatomaceous earth in an amount of 300 g was, and the mixture obtained was further allowed to dry milling process using a horizontal jet mill (diameter: 3.5 inches) to prepare a wettable powder formulation.

Example 9

The compound No. 1 in Table 1 in an amount of 160 g, tristyryl phenyl ether added thereon with oxyethylene in an amount of 40 g, sodium polycarboxylate in an amount of 20 g, glycerol in an amount of 100 g, silicon-containing defoamer in an amount of 10 g and sorbitan trioleate in an amount of 150 g were added to distilled water in an amount of 620 g and then mixed, and the mixture obtained was then allowed to wet milling process using Eiger Motor Mill (Produced by Eiger Japan K.K.), wherein zircon beads with a diameter of 1 mm are used, to prepare a suspension concentrate.

Example 10

The compound No. 1 in Table 1 in an amount of 110 g was admixed with a sodium alyklnaphthalenesulfonate in an amount of 25 g, sodium dodecylbenzenesulfonate in an amount of 20 g, sodium ligninsulfonate in an amount of 70 g, a formaldehyde condensate of a sodium alkylnaphthalenesulfonate in an amount of 140 g and sodium chloride in an amount of 185 g, sorbitan trioleate in an amount of 100 g and sorbitan trioleate added thereon with oxyethylene in an amount of 50 g, both of which are adsorbed to diatomaceous earth in an amount of 300 g, then the mixture obtained was allowed to dry milling process using a horizontal jet mill (diameter: 3.5 inches). The pulverized product was then added with distilled water in an amount of 250 g, kneaded by using Bench Kneader (Manufactured by Irie Shokai K.K.) and prepared into noodle-shaped wet granules having a diameter of 0.6 mm by using Micro-type Granulating Machine (Manufactured by Tsutsui Rikagaku Kikai K.K.).

The granules obtained was then dried by using a fan dryer at 40° C. for 12 hours to obtain a water dispersible granule.

Reference Example 1

Triflumizole in an amount of 160 g was dissolved in a mixed solvent of a petrolic solvent, Solvesso 150 in an amount of 620 g and cyclohexanone in an amount of 100 g, and the solution obtained was further added with nonyl phenyl ether added thereon with oxyethylene in an amount of 100 g and calcium dodecylbenzenesulfonate in an amount of 20 g and was dissolved while heating to prepare an emulsifiable concentrate.

Reference Example 2

Triflumizole in an amount of 160 g was dissolved in a mixed solvent of a petrolic solvent, Solvesso 150 in an amount of 570 g and cyclohexanone in an amount of 100 g, and the solution obtained was further added with nonyl phenyl ether added thereon with oxyethylene in an amount of 100 g, calcium dodecylbenzenesulfonate in an amount of 20 g and sorbitan trioleate in an amount of 50 g and was dissolved while heating to prepare an emulsifiable concentrate.

Reference Example 3

Triflumizole in an amount of 110 g was dissolved in a petrolic solvent, Solvesso 150 in an amount of 330 g, and the solution obtained was further added with sorbitan trioleate added thereon with oxyethylene in an amount of 80 g and calcium dodecylbenzenesulfonate in an amount of 10 g and was then dissolved while heating. The solution obtained was added into distilled water in an amount of 420 g wherein glycerol in an amount of 50 g being dissolved, and the mixture was then emulsified by using Polytron to prepare an emulsion.

Reference Example 4

Triflumizole in an amount of 160 g was admixed with sodium dioctylsulfosuccinate in an amount of 30 g, sodium ligninsulfonate in an amount of 100 g, clay in an amount of 460 g, diatomaceous earth in an amount of 150 g and silicon oxide in an amount of 100 g, and the mixture obtained was allowed to dry milling process using a horizontal jet mill (diameter: 3.5 inches) to prepare a wettable powder formulation.

Reference Example 5

Triflumizole in an amount of 160 g, tristyryl phenyl ether added thereon with oxyethylene in an amount of 40 g, sodium polycarboxylate in an amount of 20 g, glycerol in an amount of 100 g and a silicon-containing defoamer in an amount of 10 g were added to distilled water in an amount of 670 g and then mixed, and the mixture obtained was then allowed to wet milling process using Eiger Motor Mill (Produced by Eiger Japan K.K.), wherein zircon beads with a diameter of 1 mm are used, to prepare a suspension concentrate.

Reference Example 6

Triflumizole in an amount of 160 g, tristyryl phenyl ether added thereon with oxyethylene in an amount of 40 g, sodium polycarboxylate in an amount of 20 g, glycerol in an amount of 100 g, a silicon-containing defoamer in an amount of 10 g and sorbitan trioleate in an amount of 50 g were added to distilled water in an amount of 620 g and then mixed, and the mixture obtained was then allowed to wet milling process using Eiger Motor Mill (Produced by Eiger Japan K.K.), wherein zircon beads with a diameter of 1 mm are used, to prepare a suspension concentrate.

Reference Example 7

Triflumizole in an amount of 330 g was admixed with sodium dodecylbenzenesulfonate in an amount of 300 g, a formaldehyde condensate of a sodium alkylnaphthalenesulfonate in an amount of 70 g, sodium ligninsulfonate in an amount of 60 g, a mixture of a calcium salt and a sodium salt of a higher fatty acid in an amount of 5 g, sodium chloride in an amount of 205 g and diatomaceous earth in an amount of 300 g, then the mixture was allowed to dry milling process using a horizontal jet mill (diameter: 3.5 inches). The milled product was then added with distilled water in an amount of 330 g, kneaded by using Bench Kneader (Manufactured by Irie Shokai K.K.) and prepared into noodle-shaped wet granules having a diameter of 0.6 mm by using Micro-type Granulating Machine (Manufactured by Tsutsui Rikagaku Kikai K.K.). The granules obtained was then dried by using a fan dryer at 40° C. for 12 hours to obtain a water dispersible granule.

Reference Example 8

The compound No. 1 in Table 1 in an amount of 110 g was dissolved in a mixed solvent of a petrolic solvent, Solvesso 200 in an amount of 670 g and N-methylpyrrolidone in an amount of 100 g, and the solution obtained was further added with tristyryl phenyl ether added thereon with oxyethylene in an amount of 100 g and tristyryl phenyl ether phosphate added thereon with oxyethylene in an amount of 20 g, and was dissolved while heating to prepare an emulsifiable concentrate.

Reference Example 9

The compound No. 1 in Table 1 in an amount of 55 g was dissolved in a petrolic solvent, Solvesso 200 in an amount of 330 g, and the solution obtained was further added with tristyryl phenyl ether added thereon with oxyethylene in an amount of 100 g, and was dissolved while heating. The solution thus obtained was then added into distilled water in an amount of 415 g wherein glycerol in an amount of 100 g being dissolved, and the resulting mixture was emulsified by using Polytron to prepare an emulsion.

Reference Example 10

The compound No. 1 in Table 1 in an amount of 110 g was admixed with sodium laurylsulfate in an amount of 70 g, sodium ligninsulfonate in an amount of 100 g, a formaldehyde condensate of a sodium alkylnaphthalene sulfonate in an amount of 50 g, clay in an amount of 370 g and diatomaceous earth in an amount of 300 g, and the mixture obtained was then allowed to dry milling process using a horizontal jet mill (diameter: 3.5 inches) to prepare a wettable powder formulation.

Reference Example 11

The compound No. 1 in Table 1 in an amount of 110 g, tristyryl phenyl ether added thereon with oxyethylene in an amount of 40 g, sodium polycarboxylate in an amount of 20 g, glycerol in an amount of 100 g and a silicon-containing defoamer in an amount of 10 g were added into distilled water in an amount of 720 g and mixed, and the mixture obtained was then allowed to wet milling process using Eiger Motor Mill (Produced by Eiger Japan K.K.), wherein zircon beads with a diameter of 1 mm are used, to prepare a suspension concentrate.

Reference Example 12

The compound No. 1 in Table 1 in an amount of 110 g was admixed wotu a sodium alkylnaphthalenesulfonate in an amount of 25 g, sodium dodecylbenzenesulfonate in an amount of 20 g, sodium ligninsulfonate in an amount of 70 g, a formaldehyde condensate of a sodium alkylnaphthalenesulfonate in an amount of 140 g, sodium chloride in an amount of 335 g and diatomaceous earth in an amount of 300 g, then the mixture was allowed to dry milling process using a horizontal jet mill (diameter: 3.5 inches). The milled product was then added with distilled water in an amount of 330 g, kneaded by using Bench Kneader (Manufactured by Irie Shokai K.K.) and prepared into noodle-shaped wet granules having a diameter of 0.6 mm by using Micro-type Granulating Machine (Manufactured by Tsutsui Rikagaku Kikai K.K.). The granules obtained was then dried by using a fan dryer at 40° C. for 12 hours to obtain a water dispersible granule.

(Advantageous Effect of the Invention)

Test Example

Each of the pesticide compositions according to the present invention were diluted with tap water, respectively, and 0.5 µl each of the dilution was repeatedly applied onto a cucumber leaf (Surface area in one side: 100 cm²) up to a total volume of 100 µl by using a microsylinge, respectively. The cucumber leaf applied with the dilution of a pesticide composition was tilted 30 degrees and placed into an artificial raindrop generator DIK-600 (Manufactured by Daiki Rika Kogyo K.K.) and then subjected to rainfall at a rate of 30 ml/hour for 2 hours. After naturally drying the cucumber leaves, an extraction with acetonitrile was made from each of the applied-leaves, respectively, to determine the adsorbed-amount of triflumizole on the leaves by means of high pressure (performance) liquid chromatography, by which a remaining ratio (Adsorbed-amount of triflumizole after rainfall÷Adsorbed-amount of triflumizole before rainfall×100) of triflumizole in each pesticide composition was obtained, respectively.

TABLE 2

| Tests | Remaining Ratio |
| --- | --- |
| Example 1 | 65 |
| Example 2 | 75 |
| Example 3 | 68 |
| Example 4 | 88 |
| Example 5 | 71 |
| Example 6 | 55 |
| Example 7 | 57 |
| Example 8 | 62 |
| Example 9 | 77 |
| Example 10 | 60 |
| Reference Example 1 | 32 |
| Reference Example 2 | 30 |
| Reference Example 3 | 24 |
| Reference Example 4 | 24 |
| Reference Example 5 | 42 |
| Reference Example 6 | 40 |
| Reference Example 7 | 18 |
| Reference Example 8 | 21 |

TABLE 2-continued

| Tests | Remaining Ratio |
| --- | --- |
| Reference Example 9 | 23 |
| Reference Example 10 | 36 |
| Reference Example 11 | 39 |
| Reference Example 12 | 41 |

It can be clearly seen that the pesticide compositions of the present invention, all of which contain high content of sorbitan trioleate, show to have remarkably-improved raindrop resistance in comparison with pesticide compositions which do not contain sorbitan trioleate.

Based on the raindrop resistance of a pesticidal component on plant leaves described above, the present invention is useful to provide pesticide compositions having excellent long-lasting efficacy.

What is claimed is:

1. A raindrop resistant emulsifiable concentrate comprising 0.1–70% by weight of a pesticidal component, 1–30% by weight of an emulsifier selected from the group consisting of alkl phenyl ether polyoxyethylene, alkyl ether polyoxyethylene, and fatty acid ester polyethylene, 10–50% by weight of sorbitan trioleate and a solvent, relative to the weight of the emulsifiable concentrate.

2. A raindrop resistant emulsion comprising 0.1–70% by weight of a pesticidal component, 1–30% by weight of an emulsifier, selected from the group consisting of alkyl phenyl ether polyoxyethylene, alkyl ether polyoxyethylene, and fatty acid ester polyethylene, 10–50% by weight of sorbitan trioleate, water and a nonpolar solvent, relative to the weight of the emulsion.

3. A raindrop resistant wettable powder comprising 0.1–70% by weight of a pesticidal component, 0.1–10% by weight of a wetting agent selected from the group consisting of alkylnaphthalene sulfonate, alkylbenzenesulfonate, tristyryl phenyl ether polyoxyethylene, polycarboxylate, liginsulfonate, isobutylene-maleic anhydride, and alkylnaphthalene sulfonate formaldehyde, 0.5–20% by weight of a dispersing agent selected from the group consisting of alkylnaphthalene sulfonate, alkylbenzenesulfonate, tristyryl phenyl ether polyoxyethylene, polycarboxylate, liginsulfonate, isobutylene-maleic anhydride, and alkylnaphthalene sulfonate formaldehyde, 10–30% by weight of sorbitan trioleate and a filler, relative to the weight of the wettable powder.

4. The raindrop resistant wettable powder according to claim 3 comprising a pesticidal component, a wetting agent selected from the group consisting of alklylnaphthalene sulfonate, alkylbenzenesulfonate, tristyryl phenyl ether polyoxyethylene, polycarboxylate, liginsulfonate, isobutylene-maleic anhydride, and alkylnaphthalene sulfonate formaldehyde, a dispersing agent selected from the group consisting of alkylnaphthalene sulfonate, alkylbenzenesulfonate, tristyryl phenyl ether polyoxyethylene, polycarboxylate, liginsulfonate, isobutylene-maleic anhydride, and alkylnaphthalene sulfonate formaldehyde, a dispersing agent selected from the group consisting of alkylnaphthalene sulfonate, alkylbenzenesulfonate, tristyryl phenyl ether polyoxyethylene, polycarboxylate, liginsulfonate, isobutylene-maleic anhydride, and alkylnaphthalene sulfonate formaldehyde, a filler and sorbitan trioleate being adsorbed to a filler having high oil-absorbent property, and the average particle size of the pesticidal component therein is 20 µm or less.

5. A raindrop resistant suspension concentrate comprising 0.1–70% by weight of a pesticidal component, 0.1–10% by weight of a wetting agent selected from the group consisting of alkylnaphthalene sulfonate, alkylbenzenesulfonate, tristyryl phenyl ether polyoxyethylene, polycarboxylate, liginsulfonate, isobutylene-maleic anhydride, and alkylnaphthalene sulfonate formaldehyde, 0.5–20% by weight of a dispersing agent selected from the group consisting of alkylnaphthalene sulfonate, alkylbenzenesulfonate, tristyryl phenyl ether polyoxyethylene, polycarboxylate, liginsulfonate, isobutylene-maleic anhydride, and alkylnaphthalene sulfonate formaldehyde, 10–50% by weight of sorbitan trioleate and water, relative to the weight of the suspension concentrate.

6. The raindrop resistant suspension concentrate according to claim 5 comprising in a pesticidal component, a wetting agent, a dispersing agent, sorbitan trioleate and water, wherein the average particle size of the pesticidal component is 10 μm or less and sorbitan trioleate is contained in emulsified state.

7. A raindrop water dispersible granule comprising 0.1–70% by weight of a pesticidal component, 0.1–10% by weight of a wetting agent selected from the group consisting of alkylnaphthalene sulfonate, alkylbenzenesulfonate, tristyryl phenyl ether polyoxyethylene, polycarboxylate, liginsulfonate, isobutylene-maleic anhydride, and alkylnaphthalene sulfonate formaldehyde, 0.5–20% by weight of a dispersing agent selected from the group consisting of alkylnaphthalene sulfonate, alkylbenzenesulfonate, tristyryl phenyl ether polyoxyethylene, polycarboxylate, liginsulfonate, isobutylene-maleic anhydride, and alkylnaphthalene sulfonate formaldehyde, 10–30% by weight of sorbitan trioleate and a filler, relative to the weight of the water dispersible granule.

8. The raindrop water dispersible granule according to claim 7 comprising in that it contains a pesticidal component, of which particles are milled to an average size of 20 μm or less, a wetting agent, a dispersing agent, a filler and sorbitan trioleate, and is prepared by spray dryer method.

9. The raindrop resistant water dispersible granule according to claim 7 prepared by admixing a pesticidal component, of which particles are milled to an average size of 20 μm or less, a wetting agent, a dispersing agent, a filler and sorbitan trioleate adsorbed to a filler with high oil-absorbent property, and granulating by either agitation method or extrusion method.

10. A raindrop resistant emulsifiable concentrate according to claim 1 wherein the pesticidal component is triflumizole or a benzamidoxime compound represented by a general formula;

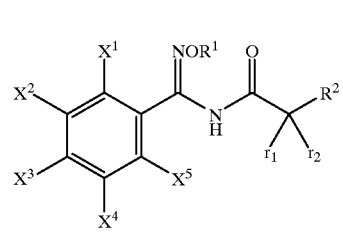

(I)

wherein $R^1$ is optionally substituted $C_1$–$C_4$ alkyl, optionally substituted $C_2$–$C_4$ alkenyl or optionally substituted $C_2$–$C_4$ alkynyl, $R^2$ is optionally substituted phenyl or optionally substituted heterocycle, $X^1$ is $C_1$–$C_4$ haloalkyl, $X^2$, $X^3$, $X^4$ and $X^5$ are each independently hydrogen, a halogen atom, $C_1$–$C_4$ alkyl, $C_1$–$C_4$ haloalkyl, $C_1$–$C_4$ alkoxy, $C_1$–$C_4$ haloalkoxy, $C_1$–$C_4$ alkylthio, $C_1$–$C_4$ alkylsulfinyl, $C_1$–$C_4$ alkylsulfonyl, nitro, amino or $C_1$–$C_4$ alkylcarbonylamino, $r_1$ and $r_2$ are each independently hydrogen, a halogen atom, $C_1$–$C_4$ alkyl, $C_1$–$C_4$ haloalkyl, $C_1$–$C_4$ alkoxy, $C_1$–$C_4$ alkylthio or amino, or $r_1$ and $r_2$ may jointly form a carbonyl group.

11. The emulsifiable concentrate according to claim 10 wherein $R^1$ is optionally substituted $C_1$–$C_4$ alkyl, $R^2$ is optionally substituted phenyl, $X^1$ is $C_1$–$C_4$ haloalkyl, $X^2$, $X^3$, $X^4$ and $X^5$ are each independently hydrogen or halogen, and $r_1$ and $r_2$ are each hydrogen.

* * * * *